(12) United States Patent
Erhardt et al.

(10) Patent No.: US 9,315,443 B2
(45) Date of Patent: Apr. 19, 2016

(54) LIQUID CATION EXCHANGER

(75) Inventors: Frank Erhardt, Bielefeld (DE);
Thomas Haas, Muenster (DE); Martin Roos, Haltern am See (DE); Daniel Demicoli, Essen (DE); Markus Poetter, Muenster (DE); Anja Schubert, Raesfeld-Erle (DE); Jan Christoph Pfeffer, Hanau (DE); Thomas Tacke, Alzenau (DE); Harald Haeger, Luedinghausen (DE); Andreas Pfennig, Kalsdorf bei Graz (AT); Marie-Dominique Przybylski-Freund, Wuerselen (DE)

(73) Assignee: Evonik Degussa GmbH, Essen (DE)

( * ) Notice: Subject to any disclaimer, the term of this patent is extended or adjusted under 35 U.S.C. 154(b) by 229 days.

(21) Appl. No.: 14/000,067

(22) PCT Filed: Dec. 1, 2011

(86) PCT No.: PCT/EP2011/071491
§ 371 (c)(1),
(2), (4) Date: Oct. 24, 2013

(87) PCT Pub. No.: WO2012/110124
PCT Pub. Date: Aug. 23, 2012

(65) Prior Publication Data
US 2014/0039210 A1    Feb. 6, 2014

(30) Foreign Application Priority Data
Feb. 16, 2011   (EP) .................................. 11154707

(51) Int. Cl.
*C07C 227/00* (2006.01)
*C07C 67/62* (2006.01)
(Continued)

(52) U.S. Cl.
CPC ............ *C07C 67/62* (2013.01); *B01D 11/0492* (2013.01); *B01J 39/04* (2013.01);
(Continued)

(58) Field of Classification Search
CPC .... C07C 67/62; C07C 227/40; C07C 229/08; B01D 11/0492; B01J 39/04; B01J 39/16; C02F 1/26; C02F 2001/425; C02F 2101/34
USPC .......................................................... 554/114
See application file for complete search history.

(56) References Cited

U.S. PATENT DOCUMENTS

| 5,248,720 A | 9/1993 | Deguchi et al. |
| 6,171,501 B1 | 1/2001 | Eyal et al. |

(Continued)

FOREIGN PATENT DOCUMENTS

| DE | 199 19 490 A1 | 11/2000 |
| JP | 54-55530 | 5/1979 |

(Continued)

OTHER PUBLICATIONS

International Search Report issued Apr. 26, 2012 in PCT/EP2011/071491.

(Continued)

*Primary Examiner* — Deborah D Carr
(74) *Attorney, Agent, or Firm* — Oblon, McClelland, Maier & Neustadt, L.L.P

(57) ABSTRACT

The invention relates to a method for removing an organic compound having one or more positive charges from an aqueous solution. Said method consists of the following steps a) the aqueous solution containing the organic compound, and a hydrophobic organic solution which contains a hydrophobic liquid cation exchanger having one or more negative charges and a negative total charge, are provided, b) the aqueous solution and the organic solution are brought into contact with each other and c) the organic solution is separated from the aqueous solution.

18 Claims, 5 Drawing Sheets

(51) Int. Cl.
*B01D 11/04* (2006.01)
*B01J 39/04* (2006.01)
*B01J 39/16* (2006.01)
*C07C 227/40* (2006.01)
*C07C 229/08* (2006.01)
*C02F 1/26* (2006.01)
*C02F 1/42* (2006.01)
*C02F 101/34* (2006.01)

(52) U.S. Cl.
CPC .............. *B01J 39/16* (2013.01); *C07C 227/40* (2013.01); *C07C 229/08* (2013.01); *C02F 1/26* (2013.01); *C02F 2001/425* (2013.01); *C02F 2101/34* (2013.01)

(56) References Cited

U.S. PATENT DOCUMENTS

| | | | |
|---|---|---|---|
| 6,620,970 | B2 | 9/2003 | Schiffer et al. |
| 6,639,108 | B2 | 10/2003 | Schiffer et al. |
| 6,764,671 | B2 | 7/2004 | Haas et al. |
| 6,861,540 | B2 | 3/2005 | Herwig et al. |
| 6,878,836 | B2 | 4/2005 | Haas et al. |
| 7,005,528 | B2 | 2/2006 | Haas et al. |
| 7,030,052 | B2 | 4/2006 | Stochniol et al. |
| 7,049,450 | B2 | 5/2006 | Hofen et al. |
| 7,091,384 | B2 | 8/2006 | Jaeger et al. |
| 7,507,862 | B2 | 3/2009 | Stochniol et al. |
| 7,879,938 | B2 | 2/2011 | Häger et al. |
| 8,399,658 | B2 | 3/2013 | Hengstermann et al. |
| 8,404,470 | B2 | 3/2013 | Thum et al. |
| 8,445,720 | B2 | 5/2013 | Hannen et al. |
| 8,703,451 | B2 | 4/2014 | Haas et al. |
| 8,703,993 | B2 | 4/2014 | Hannen et al. |
| 8,809,576 | B2 | 8/2014 | Schraven et al. |
| 8,835,691 | B2 | 9/2014 | Klasovsky et al. |
| 8,946,463 | B2 | 2/2015 | Klasovsky et al. |
| 8,981,159 | B2 | 3/2015 | Klasovsky et al. |
| 8,999,684 | B2 | 4/2015 | Poetter et al. |
| 9,000,223 | B2 | 4/2015 | Micoine et al. |
| 2002/0087036 | A1 | 7/2002 | Haas et al. |
| 2002/0158020 | A1 | 10/2002 | Maass et al. |
| 2003/0212298 | A1 | 11/2003 | Brasse et al. |
| 2010/0068773 | A1 | 3/2010 | Marx et al. |
| 2010/0266518 | A1 | 10/2010 | Springer et al. |
| 2010/0291644 | A1 | 11/2010 | Marx et al. |
| 2010/0324257 | A1 | 12/2010 | Karau et al. |
| 2011/0118433 | A1 | 5/2011 | Poetter et al. |
| 2011/0118504 | A1 | 5/2011 | Haas et al. |
| 2011/0171702 | A1 | 7/2011 | Reinecke et al. |
| 2011/0251399 | A1 | 10/2011 | Dingerdissen et al. |
| 2012/0034665 | A1 | 2/2012 | Haas et al. |
| 2012/0315366 | A1 | 12/2012 | Zehnacker et al. |
| 2013/0052700 | A1 | 2/2013 | Poetter et al. |
| 2013/0164797 | A1 | 6/2013 | Gielen et al. |
| 2013/0165672 | A1 | 6/2013 | Klasovsky et al. |
| 2013/0165685 | A1 | 6/2013 | Hannen et al. |
| 2014/0039071 | A1 | 2/2014 | Thum et al. |
| 2014/0141478 | A1 | 5/2014 | Schaffer et al. |
| 2014/0178948 | A1 | 6/2014 | Schaffer et al. |
| 2015/0010968 | A1 | 1/2015 | Engel et al. |
| 2015/0044744 | A1 | 2/2015 | Pfeffer et al. |
| 2015/0111253 | A1 | 4/2015 | Schaffer et al. |

FOREIGN PATENT DOCUMENTS

| | | | |
|---|---|---|---|
| JP | | 2-102261 | 4/1999 |
| WO | WO 98/02411 | A1 | 1/1998 |
| WO | WO 9802411 | A1 * | 1/1998 |
| WO | WO 2008/148640 | A1 | 12/2008 |
| WO | WO 2011/036000 | A1 | 3/2011 |
| WO | WO 2011/157573 | A2 | 12/2011 |
| WO | WO 2011/157573 | A3 | 12/2011 |
| WO | WO 2012/004069 | A1 | 1/2012 |
| WO | WO 2012/031884 | A1 | 3/2012 |
| WO | WO 2012/110125 | A1 | 8/2012 |
| WO | WO 2012/110126 | A1 | 8/2012 |
| WO | WO 2012/171666 | A1 | 12/2012 |
| WO | WO 2013/011018 | A1 | 1/2013 |
| WO | WO 2013/020839 | A1 | 2/2013 |
| WO | WO 2013/024111 | A1 | 2/2013 |
| WO | WO 2013/024114 | A2 | 2/2013 |

OTHER PUBLICATIONS

Diana M. Temple, "Liquid Ion-exchange Extraction of some Physiologically Active Amines" Nature, vol. 209, No. 5024, XP002637507 Feb. 12, 1966, pp. 714-715.
U.S. Appl. No. 14/126,607, filed Dec. 16, 2013, Haas, et al.
U.S. Appl. No. 14/238,576, filed Feb. 12, 2014, Schaffer, et al.
U.S. Appl. No. 14/238,591, filed Feb. 12, 2014, Schaffer, et al.
U.S. Appl. No. 14/233,505, filed Jan. 17, 2014, Poetter, et al.
U.S. Appl. No. 14/237,121, filed Feb. 4, 2014, Haas, et al.
U.S. Appl. No. 14/380,483, filed Aug. 22, 2014, Schiemann, et al.
U.S. Appl. No. 14/367,610, filed Jun. 20, 2014, Haas, et al.
U.S. Appl. No. 14/435,339, filed Apr. 13, 2015, Engel, et al.
U.S. Appl. No. 14/419,580, filed Feb. 4, 2015, Erhardt, et al.
U.S. Appl. No. 14/763,378, filed Jul. 24, 2015, Haas, et al.
U.S. Appl. No. 14/649,414, filed Jun. 3, 2015, Schaffer et al.

* cited by examiner

LIQUID CATION EXCHANGER

CROSS REFERENCE TO RELATED APPLICATIONS

The present application is a 35 U.S.C. §371 national stage patent application of International patent application PCT/EP2011/071491, filed on Dec. 1, 2011, published as WO/2012/110124 on Aug. 23, 2012, the text of which is incorporated by reference, and claims the benefit of the filing date of European application no. 11154707.1, filed on Feb. 16, 2011, the text of which is also incorporated by reference.

The present application relates to a method for removing an organic compound having one or more positive charges from an aqueous solution, comprising the steps a) providing the aqueous solution containing the organic compound and a hydrophobic organic solution, which comprises a liquid cation exchanger, wherein the liquid cation exchanger is hydrophobic, b) contacting the aqueous solution and the organic solution, and c) separating the organic solution from the aqueous solution, wherein the organic compound is a compound of the formula $NH_3^+$-A-$COOR^1$, and reaction mixtures associated therewith.

A fundamental problem in the biotechnological production of fine chemicals starting from renewable raw materials, which conventionally are synthesized starting from fossil fuels, is to transfer the product once obtained, which is typically present in a large-volume aqueous phase, to an organic phase. This transfer is carried out on the one hand in order to concentrate a finished intermediate or end product and optionally also to make synthetic processing possible in subsequent reaction steps in organic solution, and on the other hand to improve the yield of the reaction in the aqueous phase by removing the desired product or to make it possible for the reaction to be carried out at all on a technically sensible scale. As a rule, direct thermal concentration of the product, which is often present in low concentrations, from the large-volume aqueous solution is not sensible.

The distribution of a compound in a two-phase system comprising an aqueous, hydrophilic phase and an organic, hydrophobic phase, which are immiscible, depends decisively on the physicochemical properties of the particular compound. Whereas compounds with a high proportion of or consisting exclusively of unsubstituted hydrocarbons mainly accumulate in the hydrophobic phase, compounds with a high proportion of polar groups such as heteroatom-containing functionalities and quite especially compounds with charges are present mainly or practically exclusively in the aqueous phase, which hampers transfer to an organic phase.

The distribution of a compound in the stated two-phase system after establishment of equilibrium is often described with the aid of distribution coefficients, for example according to the Nernst equation $$\alpha = c_{phase\ 1} / c_{phase\ 2},$$

A special distribution coefficient is $K_{ow}$, also called the P value, which characterizes the distribution equilibrium of a compound between an octanol and an aqueous phase:

$$K_{ow} = P = c_{octanol} / c_{water}$$

An example of a positively charged organic compound much in demand industrially is 12-aminolauric acid (ALA) and derivatives thereof, especially the methyl ester (ALAME). ALA is an important starting product in the production of polymers, for example for production of pipeline systems and nylon. Conventionally, ALA is produced starting from fossil raw materials in a process with low yield via laurolactam, which is synthesized by trimerization of butadiene, then hydrogenation with formation of cyclododecane, then oxidation to cyclododecanone, reaction with hydroxylaurin and then Beckmann rearrangement. A promising route for the biotechnological production of ALA or ALAME is described in DE10200710060705.

The prior art teaches the production of positively charged organic compounds by contacting an aqueous reaction mixture comprising a biological agent with an organic phase comprising an organic solvent. For example, DE10200710060705 describes obtaining the product ALAME by shaking with ethyl acetate from an aqueous reaction mixture. Asano et al. (2008) disclose the extraction of ALA with toluene from an aqueous reaction solution comprising an ALA synthesizing enzyme.

The problem to be solved by the present invention is therefore to develop a method of removing positively charged organic compounds, especially ω-aminocarboxylic acids, with at least one positive charge from an aqueous reaction mixture, wherein a position of the distribution equilibrium between reaction mixture and a hydrophobic organic phase used as extractant that is as advantageous as possible is desirable, i.e. the distribution equilibrium should lie as far as possible on the side of the hydrophobic organic phase.

Another problem to be solved by the invention consists of developing a method of removing organic compounds with at least one positive charge, especially ω-aminocarboxylic acids, from an aqueous solution comprising a biological agent using a hydrophobic organic phase as extractant, in which the distribution equilibrium is located as far as possible on the side of the hydrophobic organic phase.

Another problem to be solved by the invention consists of developing a method of removing organic compounds with at least one positive charge, especially ω-aminocarboxylic acids, from an aqueous solution using a hydrophobic organic solution as extractant, which impairs or slows down the growth of biotechnologically relevant microorganisms, especially *Escherichia coli*, as little as possible and/or reduces the number of cells capable of dividing and/or viable cells and/or cells with active respiration and/or metabolically and synthetically active cells as little as possible.

Finally, a problem to be solved by the invention is to devise a method of removing an organic compound with at least one positive charge, especially ω-aminocarboxylic acids, from an aqueous solution comprising a biological agent using a hydrophobic organic phase as extractant, in which all of the properties that are decisive for the yield, the overall turnover and rapid practicability of a biotechnological synthesis process on which it is based, especially the toxicity of the organic phase against the biological agent and the uptake of the compound into the organic extractant, are optimized with respect to the total yield or a faster progress or, in the case of a continuous process, usability of the biological agent for as long as possible, especially for the case when the organic compound with at least one positive charge is the product or an intermediate of the synthesis process, which is synthesized with the participation of a catalytic activity of the biological agent.

These and other problems are solved by the subject matter of the present application and especially also by the subject matter of the appended independent claims, wherein embodiments follow from the subclaims.

The problem to be solved by the invention is solved in a first aspect by a method for removing an organic compound having one or more positive charges from an aqueous solution, comprising the steps a) providing the aqueous solution containing the organic compound and a hydrophobic organic solution, which comprises a liquid cation exchanger,
   wherein the liquid cation exchanger is hydrophobic,
b) contacting the aqueous solution and the organic solution, and
c) separating the organic solution from the aqueous solution,
wherein the organic compound is a compound of formula I $$NH_3^+\text{-A-COOR}^1 \qquad (I),$$

wherein $R^1$ is hydrogen, methyl, ethyl or a negative charge and A is an unsubstituted, linear alkylene group with at least three, preferably at least eight carbon atoms,
and wherein the liquid cation exchanger is a fatty acid.

In a first embodiment of the first aspect, the problem is solved by a method according to one of Claims 1, wherein the temperature in step b) is 28 to 70, preferably 30 to 37° C.

In a second embodiment, which is also an embodiment of the first embodiment of the first aspect, the problem is solved by a method according to one of Claims 1 to 2, wherein the pH in step b) is 6 to 8, preferably 6.2 to 7.2.

In a third embodiment, which is also an embodiment of the first to second embodiment of the first aspect, the problem is solved by a method wherein the molar ratio of liquid cation exchanger to organic compound is at least 1.

In a third embodiment, which is also an embodiment of the first to third embodiment of the first aspect, the problem is solved by a method wherein the volume ratio of organic solution to aqueous solution is 1:10 to 10:1.

In a fourth embodiment, which is also an embodiment of the first to third embodiment of the first aspect, the problem is solved by a method wherein the liquid cation exchanger is a fatty acid with more than 12, preferably with 14 to 22, more preferably 16 to 18 carbon atoms.

In a fifth embodiment, which is also an embodiment of the first to fourth embodiment of the first aspect, the problem is solved by a method wherein the liquid cation exchanger is an unsaturated fatty acid, preferably oleic acid or erucic acid.

In a sixth embodiment, which is also an embodiment of the first to fifth embodiment of the first aspect, the problem is solved by a method wherein the aqueous solution furthermore comprises a biological agent with catalytic activity.

In a seventh embodiment, which is also an embodiment of the first to sixth embodiment of the first aspect, the problem is solved by a method wherein the biological agent is a cell, preferably a bacterial cell and the cell more preferably has a recombinant alkane monooxygenase, a recombinant transaminase and preferably furthermore at least one enzyme from the group comprising an alcohol dehydrogenase, an alanine dehydrogenase and the AlkL gene product or variants thereof.

In an eighth embodiment, which is also an embodiment of the first to seventh embodiment of the first aspect, the problem is solved by a method wherein the presence of the organic compound has an adverse effect on the catalytic activity, preferably in that the organic compound is a compound that is toxic to the cell.

In a ninth embodiment, which is also an embodiment of the first to eighth embodiment of the first aspect, the problem is solved by a method wherein the organic solution furthermore contains at least one organic solvent, preferably a fatty acid and/or a fatty acid ester.

In a tenth embodiment, which is also an embodiment of the first to ninth embodiment of the first aspect, the problem is solved by a method according to Claim 12, wherein the organic solution comprises as liquid cation exchanger 20 to 80 vol %, preferably 25 to 75 vol % oleic acid, and as solvent lauric acid methyl ester and the organic compound is 12-aminolauric acid methyl ester and a bacterial cell is present in the aqueous solution that has a recombinant alkane monooxygenase, a recombinant transaminase and preferably furthermore at least one enzyme from the group comprising an alcohol dehydrogenase, an alanine dehydrogenase and the AlkL gene product or variants thereof.

In a second aspect, the problem to be solved by the invention is solved by a reaction mixture comprising an aqueous solution and a hydrophobic organic solution,
   wherein the hydrophobic organic solution comprises a fatty acid, preferably a fatty acid with more than 12 carbon atoms, more preferably an unsaturated fatty acid as liquid cation exchanger,
   and wherein the aqueous solution is a compound of formula (I)

$$NH_3^+\text{-A-COOR}^1 \qquad (I),$$

wherein $R^1$ is hydrogen, methyl, ethyl or a negative charge and A is an unsubstituted, linear alkylene group with at least three, preferably at least eight carbon atoms.

In one embodiment of the second aspect, the problem to be solved by the invention is solved by a reaction mixture according to the first aspect, wherein the aqueous solution furthermore comprises a cell that has a recombinant alkane monooxygenase, a recombinant transaminase and preferably furthermore at least one enzyme from the group comprising an alcohol dehydrogenase, an alanine dehydrogenase and the AlkL gene product or variants thereof.

Further embodiments of the second aspect comprise all embodiments of the first aspect.

The problem to be solved by the invention is solved in a fourth aspect by a method for removing an organic compound having one or more positive charges from an aqueous solution, comprising the steps:
a) providing the aqueous solution containing the organic compound and a hydrophobic organic solution, which comprises a liquid cation exchanger,
   wherein the liquid cation exchanger is hydrophobic,
   and wherein the liquid cation exchanger has one or more negative charges and a negative total charge,
b) contacting the aqueous solution and the organic solution, and
c) separating the organic solution from the aqueous solution.

In a second embodiment of the fourth aspect of the present invention, which also represents an embodiment of the first embodiment of the present invention, the method comprises the step:
d) working-up the organic solution, preferably by backwash of the organic compound into another aqueous solution.

In a third embodiment of the fourth aspect of the present invention, which also represents an embodiment of the first to second embodiment of the present invention, the temperature in step b) of the method according to the invention is 28 to 70° C., preferably 30 to 37° C.

In a fourth embodiment of the fourth aspect of the present invention, which also represents an embodiment of the first to third embodiment of the present invention, the pH in step b) of the method according to the invention is 3 to 8, preferably 6 to 8, especially preferably 6.2 to 7.2.

In a fifth embodiment of the fourth aspect of the present invention, which also represents an embodiment of the first to fourth embodiment of the present invention, the molar ratio of liquid cation exchanger to organic compound in the method is at least 1.

In a sixth embodiment of the fourth aspect of the present invention, which also represents an embodiment of the first to fifth embodiment of the present invention, the volume ratio of organic solution to aqueous solution is 1:10 to 10:1.

In a seventh embodiment of the fourth aspect of the present invention, which also represents an embodiment of the first to sixth embodiment of the present invention, the organic compound has at least one positively charged substituent of formula (I)

$$—N^+R^2R^3R^4 \qquad (I)$$

or, if at least one substituent from the group comprising $R^2$, $R^3$ and $R^4$ is hydrogen, the unprotonated form thereof,
wherein $R^2$, $R^3$ and $R^4$ are selected independently of one another from the group comprising hydrogen, methyl, ethyl, propyl, 2-propyl, butyl, t-butyl, pentyl, hexyl, benzyl, hydroxyl, substituted or unsubstituted and/or linear or branched or cyclic alkyl or alkenyl.

In an eighth embodiment of the fourth aspect of the present invention, which also represents an embodiment of the first to seventh embodiment of the present invention, the organic compound has the formula (II)

$$Z-A-N^+R^2R^3R^4 \qquad (II)$$

or, if at least one substituent from the group comprising $R^2$, $R^3$ and $R^4$ is hydrogen, the unprotonated form thereof,
wherein $R^2$, $R^3$ and $R^4$ are selected independently of one another from the group comprising hydrogen, methyl, ethyl, propyl, 2-propyl, butyl, t-butyl, pentyl, hexyl, benzyl, hydroxyl, substituted or unsubstituted and/or linear or branched or cyclic alkyl or alkenyl,
wherein A represents a hydrocarbon chain comprising at least three carbon atoms, preferably an unsubstituted alkenyl group,
and wherein Z is selected from the group that comprises —COOH, —COOR⁵, —COH, —CH₂OH and unprotonated forms thereof,
wherein $R^5$ is selected from the group comprising hydrogen, methyl, ethyl, propyl, 2-propyl, butyl, t-butyl, pentyl, hexyl, benzyl, hydroxyl, substituted or unsubstituted and/or linear or branched or cyclic alkyl or alkenyl.

In a ninth embodiment of the fourth aspect of the present invention, which also represents an embodiment of the first to eighth embodiment of the present invention, the organic compound has the formula III $$NH_3^+-A-COOR^1 \qquad (III),$$

or an unprotonated form thereof, wherein $R^1$ is hydrogen, methyl or ethyl and A is an unsubstituted, linear alkylene group with at least three carbon atoms.

In a tenth embodiment of the fourth aspect of the present invention, which also represents an embodiment of the first to ninth embodiment of the present invention, the liquid cation exchanger has at least one alkyl or alkenyl group with at least six carbon atoms and a terminal substituent from the group comprising —COOH, —OSO₂H, —OPO(OH)₂— and —OPO(OH)O— and unprotonated forms thereof.

In an eleventh embodiment of the fourth aspect of the present invention, which also represents an embodiment of the first to tenth embodiment of the present invention, the liquid cation exchanger is an unsaturated fatty acid, preferably oleic acid.

In a twelfth embodiment of the fourth aspect of the present invention, which also represents an embodiment of the first to eleventh embodiment of the present invention, the aqueous solution furthermore comprises a biological agent with catalytic activity.

In a thirteenth embodiment of the fourth aspect of the present invention, which also represents an embodiment of the first to twelfth embodiment of the present invention, the biological agent is a cell, preferably a bacterial cell.

In a fourteenth embodiment of the fourth aspect of the present invention, which also represents an embodiment of the first to thirteenth embodiment of the present invention, the presence of the organic compound has an adverse effect on the catalytic activity.

In a fifteenth embodiment of the fourth aspect of the present invention, which also represents an embodiment of the first to fourteenth embodiment of the present invention, the organic solution furthermore contains at least one organic solvent, preferably a fatty acid and/or a fatty acid ester.

In a sixteenth embodiment of the fourth aspect of the present invention, which also represents an embodiment of the first to fifteenth embodiment of the present invention, the organic solution comprises, as liquid cation exchanger, 20 to 80 vol %, preferably 25 to 75 vol % of oleic acid, and lauric acid methyl ester as solvent, and the organic compound is 12-aminolauric acid methyl ester and in the aqueous solution a bacterial cell is present that has a catalytic activity involved in the synthesis of 12-aminolauric acid methyl ester.

In a fifth aspect, the problem to be solved by the invention is solved by a bioreactor comprising an aqueous solution, comprising a biological agent, and a hydrophobic organic solution comprising a liquid cation exchanger. In a preferred embodiment of the present invention, the term "bioreactor", as used herein, means any vessel in which biotechnologically usable microorganisms are cultured in controlled conditions and/or can be used for a biotechnological process, preferably the synthesis of an organic compound.

In a second embodiment of the fifth aspect, which is also an embodiment of the first embodiment of the third aspect of the present invention, the liquid cation exchanger is a fatty acid, preferably oleic acid.

In a third embodiment of the fifth aspect, which is also an embodiment of the first to second embodiment of the third aspect of the present invention, the hydrophobic organic solution furthermore comprises a fatty acid ester, preferably lauric acid methyl ester.

In a fourth embodiment of the fifth aspect, which is also an embodiment of the first to third embodiment of the second aspect of the present invention, the hydrophobic organic solution comprises oleic acid as cation exchanger and 25 to 75 vol % lauric acid methyl ester as solvent.

In a fifth embodiment, which is also an embodiment of the first to fourth embodiment of the fifth aspect of the present invention, the organic compound is a compound according to one of the embodiments of the first aspect of the invention.

In a sixth aspect, the problem to be solved by the present invention is solved by a method of producing an organic compound with one or more positive charges, wherein the organic compound is toxic to cells, comprising culturing, in an aqueous solution, cells involved in the synthesis of the organic compound, preferably cells that catalyse at least one step of the synthesis, in the presence of a hydrophobic organic solution comprising a liquid cation exchanger and optionally an organic solvent.

In a second embodiment of the sixth aspect of the present invention, the organic compound is 12-aminolauric acid or methyl ester thereof, and the organic solvent is lauric acid methyl ester.

Further embodiments of the fourth, fifth and sixth aspect comprise all embodiments of the first and second aspect of the present invention.

The inventors of the present invention found that the efficiency of removing an organic compound with one or more positive charges from an aqueous solution into a hydrophobic organic solution can, surprisingly, be increased when said organic solution comprises a liquid cation exchanger. Without wishing to be bound to any theory, the inventors of the present invention presume that the negative charge or the negative charges of the liquid cation exchanger interacts/interact ionically with the one positive charge or the several positive charges of the organic compounds and that this interaction leads to a masking of at least one positive charge, which increases the solubility in the organic phase.

In a preferred embodiment, the term "liquid cation exchanger", as used herein, means a compound that is soluble in a hydrophobic organic solvent, and owing to one or more negative permanent charges is capable of entering into an ionic interaction with at least one cation. A liquid cation exchanger typically comprises at least one saturated or unsaturated hydrocarbon chain, which can be linear or branched, and a negative charged group, for example a carboxyl group. In a preferred embodiment the liquid ion exchanger is a fatty acid, in a more preferred embodiment it is an unsaturated fatty acid, for example oleic acid. In a preferred embodiment the liquid ion exchanger is di(2-ethylhexyl)phosphoric acid (also called DEHPA or D2EHPA).

In a preferred embodiment, the liquid ion exchanger not only has a negative total charge, but even no positive charge. In a preferred embodiment the term "total charge" of the ion exchanger or of some other molecule, as used herein, means the total of the charges of all functional groups bound covalently to the molecule. For example at pH 7 lauric acid has a negative charge as total charge, regardless of the presence of other molecules or counterions such as potassium ions that are present in the aqueous solution.

In a preferred embodiment of the present invention, the term "contacting", as used herein, means that two phases are exposed to one another directly and in particular without interposing a physical barrier such as a membrane. In the simplest case contacting is carried out by putting the two phases into the same vessel and mixing them together in a suitable way, for example by stirring.

In a preferred embodiment the organic compound has a positive total charge. In another preferred embodiment the organic compound has no negative charges. In a preferred embodiment the organic compound is an ω-aminocarboxylic acid.

In a preferred embodiment the term "has a charge", as used herein, means that a compound so designated has a corresponding charge in aqueous solution at pH 0 to 14, preferably 2 to 12, 2 to 6, 8 to 12, 3 to 10, 6 to 8, most preferably at pH 7. In a preferred embodiment it is a charge that is permanently present. In another preferred embodiment the term "has a charge", as used herein, means that the corresponding functional group or compound has, at pH 7, mainly the corresponding charge, i.e. to at least 50, more preferably 90 and even more preferably 99%.

In a preferred embodiment of the invention, the term "containing" is to be understood in the sense of "comprising", i.e. not concluding. A mixture containing A can in this sense have other constituents besides A. The formulation "one or more charges" means at least one charge of the corresponding nature.

In a preferred embodiment the term "hydrophobic", as used herein, means the property of a liquid to form, in the presence of an aqueous phase, its own liquid phase clearly delimited from the aqueous phase. It can be a continuous liquid phase or an emulsion. In another preferred embodiment the term "hydrophobic", as used herein, means the property of a compound of essentially not dissolving in water. Finally, in another preferred embodiment, as used herein, the term is to be understood in that a compound so designated has a P value (J. Sangster, *Octanol-Water Partition Coefficients: Fundamentals and Physical Chemistry*, Vol 2 of Wiley Series in Solution Chemistry, John Wiley & Sons, Chichester, 1997), whose common logarithm is greater than 0, preferably greater than 0.5, more preferably greater than 1 and most preferably greater than 2.

In another embodiment of the present invention, the liquid ion exchanger has no or only a moderate toxic action on biotechnologically relevant microorganisms. The term "toxic action", as used herein, means in a preferred embodiment of the invention the property of a compound, when in contact with the corresponding microorganisms, to lower their growth rate, to lower their metabolic activity, to increase their energy consumption, to lower their optical density or the number of viable cells and/or to lead directly to their dying off and lysis. In a preferred embodiment at least one of these effects of a toxic compound is already achieved at low concentration, preferably at a concentration of 1000, more preferably 100, even more preferably 50 or 25, and most preferably 5 mg/L. A person skilled in the art knows numerous methods for routine use, by means of which toxicity can be investigated. These include for example measurement of the respiration of corresponding microorganisms by means of $O_2$ electrodes or comparative plating-out of samples of microorganisms and subsequent counting of the colony-forming units (CFUs). In a preferred embodiment, "moderate toxic action" means that microorganisms that are in a growth phase continue to grow and/or are metabolically active in the presence of the compound, but to a lower extent than for a control that is incubated in the same conditions in the absence of the corresponding compound, and/or have a lengthened lag phase.

The contacting of aqueous and organic solution takes place in suitable conditions and in particular for a period that is sufficient for sufficient transfer of the organic compound from the aqueous phase into the organic phase, ideally even for establishment of the corresponding equilibrium. This time period and conditions can be determined by a person skilled in the art in routine experiments.

In an especially preferred embodiment, the organic compound having one or more positive charges is a terminally aminated fatty acid, especially preferably 12-aminolauric acid or an ester thereof or a mixture of the two compounds. A person skilled in the art will appreciate that an ester of a fatty acid can, in the presence of a biological system comprising esterase activities, partially be in the form of the corresponding acid and in this connection the two compounds are to be regarded to that extent as equivalent. Accordingly, in an especially preferred embodiment, as used herein, fatty acids or fatty acid derivatives also comprise the corresponding esters, preferably methyl ester, and vice versa.

In an especially preferred embodiment the term "alkylene group", as used herein, means a group of the formula —$(CH_2)_n$—, i.e. an alkane with two substituents that are left open, and are preferably terminal. The two substituents can be for example an amine group and a carboxyl group. In a preferred embodiment n is at least 3, more preferably at least 6, more preferably 11. In the case of a "substituted alkylene chain", at least one hydrogen atom is replaced with a substituent other than a hydrogen atom or an alkyl residue, preferably another atom such as a hydrogen atom. However, in a special embodiment the term "unsubstituted alkylene group", as used herein, means a hydrocarbon chain of the formula —$(CH_2)_n$— without said substituent.

The temperature in step b) depends not only on the properties of the liquid cation exchanger, but, especially for the case when the contacting of the aqueous and the organic solution takes place as the reaction proceeds in the aqueous phase, also on the temperature requirements of any reactions taking place in the aqueous phase. Especially for the case when a biological agent such as a living cell is catalytically active in the aqueous phase, the temperature must be suitable for maintaining this activity. In a preferred embodiment the temperature in step b) is 0 to 100° C., more preferably 20 to 80° C., 28 to 70° C., 30 to 37° C., 35 to 40° C.

The pH in step b) must also take into account the requirements of any reactions taking place simultaneously, and the stability of educts, products, intermediates or reagents. In a preferred embodiment the pH is 3 to 8, more preferably 6 to 8, even more preferably 6.2 to 7.2.

In order to transfer the organic compound from the aqueous phase into the organic phase as completely as possible, a sufficient amount of the liquid cation exchanger is required. In a preferred embodiment of the present invention the molar ratio of liquid cation exchanger and organic compound in at least one step, summed in a continuous process over the total course of the reaction, is at least 1, i.e. at least one molecule of liquid cation exchanger is used per molecule of the organic compound. In an even more preferred embodiment the ratio is greater than 2, 3, 5, 10, 15, or 20, preferably 1.5 to 3.

The volume ratio of the organic solution to the aqueous solution is, together with the cation exchanger/organic compound molar ratio, important for an efficient process. In a special embodiment it is 100:1 to 1:100, preferably 20:1 to 1:20, more preferably 10:1 to 1:10, 4:1 to 1:4, 3:1 to 1:3 or most preferably 1:2 to 2:1.

In a preferred embodiment of the present invention, a fatty acid is used as liquid cation exchanger. In a preferred embodiment of the present invention, the term "fatty acid", as used herein, means a carboxylic acid, preferably alkanoic acid, with at least 6, preferably 8, more preferably 10, most preferably 12 carbon atoms. In a preferred embodiment they are linear fatty acids, in another embodiment they are branched. In a preferred embodiment they are saturated fatty acids. In an especially preferred embodiment they are unsaturated. In another preferred embodiment it is a linear fatty acid with at least 12 carbon atoms comprising a double bond, preferably at position 9. In another preferred embodiment it is a simple unsaturated fatty acid, in which the double bond is located at position 9 and/or 11. In another preferred embodiment the liquid cation exchanger is an unsaturated fatty acid selected from the group comprising oleic acid, palmitoleic acid and gadoleic acid and icosenoic acid. In the most preferred embodiment it is oleic acid. In an especially preferred embodiment it is a fatty acid with 6, 7, 8, 9, 10, 11, 12, 13, 14, 15, 16, 17, 18, 19, 20, 21, 22, 23, 24, 25, 26, 27, 28, 29, 30 carbon atoms, preferably more than 12, more preferably more than 14 carbon atoms, even more preferably with 14 to 28, 14 to 22, most preferably 16 to 18 carbon atoms.

In another preferred embodiment a mixture of various fatty acids is used as liquid ion exchanger, for example in the form of soya oil or globe thistle oil. This comprises a preliminary hydrolysis if necessary, if the fatty acids are present as esters.

In an especially preferred embodiment of the present invention, a combination of two liquid cation exchangers, preferably with at least one of them a fatty acid, is used.

A particular advantage of the present invention is the compatibility of the method according to the invention with biotechnological processes and biological agents used therein. In a particular embodiment of the present invention, the term "biological agent with catalytic activity", as used herein, means a biocatalyst synthesized by a cell in all stages of purification, from the whole cell to the isolated molecule. In a preferred embodiment it is a cell expressing enzymes with catalytic activity. The cell can be a prokaryote, including Archaea, or a eukaryote, preferably from the group comprising *Pseudomonas, Corynebacterium* and *E. coli*. In an even more preferred embodiment the agent is a bacterial cell, even more preferably a Gram-negative bacterial cell, most preferably *E. coli*. In another preferred embodiment it is a eukaryotic cell, more preferably a fungus cell, even more preferably a yeast cell, most preferably *Saccharomyces* or *Candida, Pichia*, especially *Candida tropicalis*. The term "cell" is used, in a special embodiment, in this application as being equivalent and interchangeable with the term "microorganism". Furthermore, the cell can be an isolated cell or a mixture of cultures.

The cell used as biological agent can be viable, or it can be a preparation thereof, for example a membrane fraction or cytosolic fraction or a crude extract of the cell.

When the biological agent is an isolated molecule in various stages of purification, this can be all catalytic active molecules produced by a cell. In an especially preferred embodiment it is a molecule from the group comprising peptides, polypeptides, carbohydrates, nucleic acids or mixed forms thereof. In a more preferred embodiment it is a catalytically active polypeptide. In another preferred embodiment it is an immobilized molecule.

The catalytic functions required for synthetic biotechnological processes are varied. In a preferred embodiment the term "catalytic activity", as used herein, is a synthetic activity, i.e. the catalysis of chemical reactions comprising the formation of at least one new covalent bond. In another preferred embodiment it is a transport activity, i.e. the capacity of a molecule to effect the transport of another molecule from one compartment to another, e.g. the taking up of a substance from the aqueous medium via a cell membrane into the interior of the cell.

In an especially preferred embodiment the biological agent is a living cell, which is used for catalysis in the presence of the liquid cation exchanger, preferably in order to synthesize an organic compound with one or more positive charges, which is removed subsequently or simultaneously by means of the liquid cation exchanger into a hydrophobic organic phase.

In an especially preferred embodiment the presence of the organic compound has an adverse effect on the catalytic activity. In one embodiment this can lower the amount of activity present, which can be expressed in the sense of a lower $k_{cat}$ of an enzyme. In another embodiment the affinity of the agent having catalytic activity can be affected in the sense of an increased $K_M$ of an enzyme. In another embodiment the specificity of the catalytic activity can be altered, for example so that it preferably converts or preferably converts a substrate molecule other than that desired. In another embodiment the organic compound has a toxic action on a cell as biological agent.

In another embodiment the organic compound is an organic compound that decreases the availability of an essential co-substrate or co-enzyme. This can be the case for example when the organic compound inhibits a corresponding regeneration reaction.

In addition to the liquid cation exchanger, the hydrophobic organic phase can furthermore contain a hydrophobic solvent. This can serve for increasing the absorption capacity of a liquid cation exchanger in the hydrophobic phase and for preventing undesirable behaviour, for example flocculation. In a preferred embodiment the solvent is an educt of a reaction taking place in the aqueous solution, most preferably the substrate of an enzyme-catalysed reaction taking place in the aqueous solution. In a preferred embodiment it is a fatty acid ester. In an especially preferred embodiment the solvent is a fatty acid ester, preferably methyl ester, of a fatty acid that serves as liquid cation exchanger.

The proportion of the solvent, if present, in the hydrophobic organic phase is in a preferred embodiment 1 to 99 percent by volume (vol %). In a preferred embodiment the proportion of the solvent is 10 to 90, more preferably 20 to 80, most preferably 25 to 75 vol %.

In a most preferred embodiment of the method the organic compound is 12-aminolauric acid and/or 12-aminolauric acid methyl ester, which is or are produced in the aqueous phase by a recombinant strain of E. coli by progressive oxidation of the terminal carbon atom of lauric acid methyl ester, as is disclosed in DE10200710060705, and the hydrophobic phase comprises 25 to 75% oleic acid as liquid cation exchanger dissolved in lauric acid methyl ester as reaction substrate.

The teaching of the present invention can be carried out not only using the exact amino acid or nucleic acid sequences of the biological macromolecules described herein, but also using variants of said macromolecules, which can be obtained by deletion, addition or substitution of one or more than one amino acids or nucleic acids. In a preferred embodiment the term "variant" of a nucleic acid sequence or amino acid sequence used in the following as equivalent and interchangeable with the term "homologue", as used herein, means another nucleic acid or amino acid sequence, which with respect to the corresponding original wild-type nucleic acid or amino acid sequence has a homology, used here as equivalent to identity, of 70, 75, 80, 85, 90, 92, 94, 96, 98, 99% or a higher percentage, wherein preferably amino acids other than the amino acids forming the catalytically active centre or amino acids essential for the structure or folding are deleted or substituted or the latter are only conservatively substituted, for example a glutamate instead of an aspartate or a leucine instead of a valine. The prior art describes algorithms that can be used for calculating the extent of homology of two sequences, e.g. Arthur Lesk (2008), Introduction to bioinformatics, 3$^{rd}$ edition. In another preferred embodiment of the present invention, the variant of an amino acid or nucleic acid sequence has, preferably additionally to the aforementioned sequence homology, essentially the same enzymatic activity of the wild type molecule or original molecule. For example, a variant of a polypeptide enzymatically active as protease has the same or substantially the same proteolytic activity as the polypeptide enzyme, i.e. the capacity to catalyse the hydrolysis of a peptide bond. In a special embodiment the term "substantially the same enzymatic activity" means an activity with respect to the substrates of the wild-type polypeptide, which is well above the background activity and/or differs by less than 3, preferably 2, more preferably one order of magnitude from the $K_m$ and/or $k_{cat}$ values that the wild-type polypeptide has with respect to the same substrates. In another preferred embodiment the term "variant" of a nucleic acid or amino acid sequence comprises at least one active part/or fragment of the nucleic acid or amino acid sequence. In another preferred embodiment the term "active part", as used herein, means an amino acid sequence or a nucleic acid sequence that has a smaller length than the full length of the amino acid sequence or codes for a smaller length than the full length of the amino acid sequence, wherein the amino acid sequence or the encoded amino acid sequence with smaller length than the wild-type amino acid sequence has substantially the same enzymatic activity as the wild-type polypeptide or a variant thereof, for example as alcohol dehydrogenase, monooxygenase or transaminase. In a special embodiment the term "variant" of a nucleic acid comprises a nucleic acid, whose complementary strand, preferably under stringent conditions, binds to the wild-type nucleic acid. The stringency of the hybridization reaction can easily be determined by a person skilled in the art and generally depends on the length of the probe, the temperatures during washing and the salt concentration. In general, longer probes require higher temperatures for hybridization, whereas lower temperatures are sufficient for shorter samples. Whether hybridization takes place generally depends on the ability of the denatured DNA to annellate onto complementary strands that are present in its surroundings, and indeed below the melting point. The stringency of hybridization reaction and corresponding conditions are described in detail in Ausubel et al. 1995. In a preferred embodiment the term "variant" of a nucleic acid, as used herein, comprises any nucleic acid sequence that codes for the same amino acid sequence as the original nucleic acid or a variant of this amino acid sequence in the context of the degeneracy of the genetic code.

Suitable polypeptides that can be used for the production of organic compounds of formula (I), especially alkane monooxygenases, AlkL, transaminases, aldehyde dehydrogenases and alanine dehydrogenases are described in the prior art, for example in DE10200710060705, EPI 1004029 or in PCT/EP2011/053834.

In the most preferred embodiment the alkane monooxygenase is an alkane monooxygenase of the AlkB type. AlkB is an oxidoreductase from the AlkBGT system from Pseudomonas putida, which is known for its hydroxylase activity. It is dependent on two other polypeptides, AlkG and AlkT. AlkT is characterized as FAD-dependent rubredoxin-reductase, which transmits electrons from NADH to AlkG. AlkG is a rubredoxin, an iron-containing redox protein, which functions as direct electron donor for AlkB. In a preferred embodiment the term "alkane monooxygenase of the AlkB type", as used herein, means a membrane-bound alkane monooxidase. In another preferred embodiment the same term "alkane monooxygenase of the AlkB type" means a polypeptide with a sequence homology of increasingly preferably at least 75, 80, 85, 90, 92, 94, 96, 98 or 99% to the sequence of the AlkB of Pseudomonas putida Gpo1 (database code: CAB54050.1). In another preferred embodiment the term means a cytochrome-independent monooxygenase. In another preferred embodiment the term "alkane monooxygenase of the AlkB type" 5 means a cytochrome-independent monooxygenase, which uses at least one rubredoxin or homologue as electron donor. In an especially preferred embodiment the term means a membrane-bound, cytochrome-independent alkane monooxygenase with increasingly preferably at least 60, 70, 80, 80, 85, 90, 92, 94, 96, 98 or 99% to the sequence of the AlkB of Pseudomonas putida Gpo1, which needs as electron donor at least AlkG (CAB54052.1), but preferably the combination of AlkG with the reductase AlkT (CAB54063.1), wherein AlkG and/or AlkT can also be a homologue of the respective polypeptide. The term "sequence", as used herein, relates to the amino acid sequence of a polypeptide and/or the nucleic acid sequence encoding it. In another preferred embodiment an "alkane monooxygenase of the AlkB type", as used herein, is a cytochrome-independent oxidoreductase, i.e. an oxidoreductase that does not comprise cytochrome as cofactor.

The present invention is further illustrated by the following figures and non-limiting examples, from which further features, embodiments, aspects and advantages of the present invention can be found.

EXAMPLE 1

Figure 1:
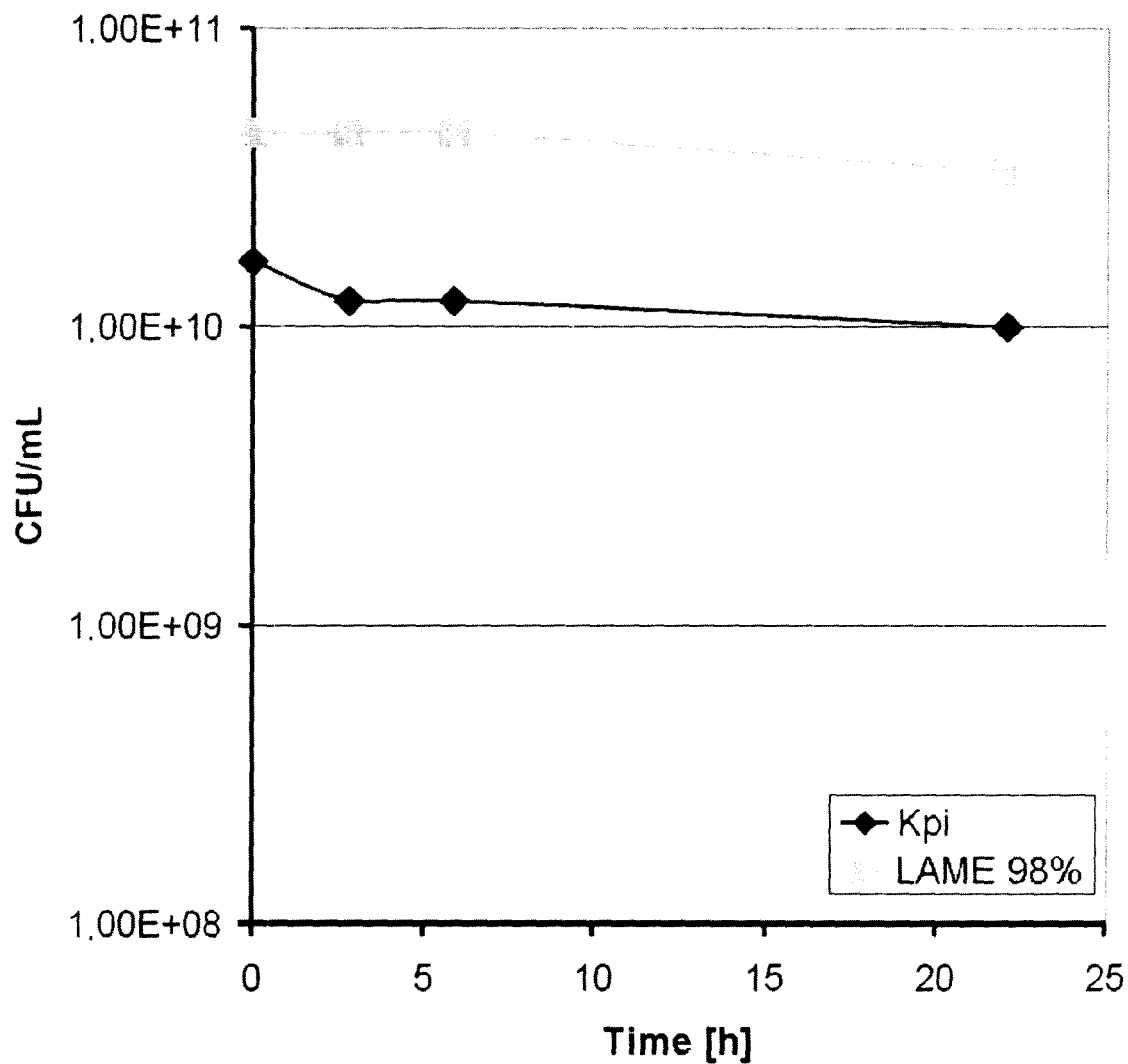
FIG. 1 shows a controlled experiment for confirming that LAME does not have toxic action, investigated with an *E. coli* W3110 strain and in comparison with potassium phosphate buffer (Kpi) as negative control.

Investigation of the Toxicity of the Solvent LAME that is Used in Compositions with Liquid Cation Exchangers This test showed the relatively low toxicity of LAME with respect to biotechnologically relevant microorganisms, which makes LAME a suitable organic solvent for the method according to the invention.

Before the determination of CFUs could be undertaken, an LB plate (10 g/L peptone from casein, 5 g/L yeast extract, 10 g/L NaCl) was streaked with *E. coli* BW3110 and incubated for 24 h. In the evening of the next day, a preculture of this previously streaked plate was inoculated. This preculture had a volume of 50 mL of LB medium, and was incubated overnight for approx. 16 h. On the next day the preculture with an $OD_{600}$ of 0.2 was inoculated in 200 mL of M9 medium ($Na_2HPO_4$ 6.79 g/L; $KH_2PO_4$ 3.0 g/L; NaCl 0.5 g/L; $NH_4Cl$ 1 g/L; 1 mL/L trace element solution, pH 7.4. Trace element solution: HCl 37% (=455.8 g/L) 36.50 g/L; $MnCl_2*7H_2O$ 1.91 g/L; $ZnSO_4*7H_2O$ 1.87 g/L; Na-EDTA*$2H_2O$ (Titriplex III) 0.84 g/L; $H_3BO_3$ 0.30 g/L; $Na_2MoO_4*2H_2O$ 0.25 g/L; $CaCl_2*2H_2O$ 4.70 g/L; $FeSO_4*7H_2O$ 17.80 g/L; $CuCl_2*2H_2O$ 0.15 g/L) with 3% glucose (w/v) and incubated for approx. 20 h. After incubation of the main culture, the cells were harvested, centrifuged at 5258 g and 4° C. for 10 min and, with an $OD_{600}$ of 30, were resuspended in 10 mL of 50 mM $Kp_i$ buffer at pH 7.4 (or 25 mM HEPES buffer pH 7.4, when CFU determinations with ALAME were carried out). Both buffer solutions used contained 5% glucose (w/v). Then the bacterial suspension was transferred to the shaking flasks and the solutions of the respective substances were added. After mixing by swirling the flask, 100 μL of the suspension was withdrawn by pipette and put into 900 μL of prepared sterile saline. This corresponded to sampling at time point $t_0$. The mixtures were then incubated at 250 rpm and 30° C. The CFUs were determined over a period of 22 h. First the samples were taken at time points $t_0$, $t_3$, $t_6$ and $t_{22}$. For some mixtures another sampling time point $t_{1.5}$ was added and furthermore another additional dilution series was plated out, in order to minimize deviations.

The $OD_{600}$ was 60. The cells were resuspended in 10 mL $Kp_i$ buffer and then mixed in the flask with 5 mL LAME 98% (w/w). One dilution step per assay was plated out. The number of CFU/mL remained constant over a period of 6 h. After 22 h, a percentage drop in the live cell count of just 30.3% was recorded.

EXAMPLE 2

Comparative Tests for Toxicity of Various Liquid Cation Exchangers to Biotechnologically Relevant Microorganisms This example shows the lower toxicity of linear fatty acids relative to other liquid cation exchangers such as DEHPA and branched and linear saturated fatty acids.

First a preculture comprising 20 ml of LB medium in a 100-ml baffle flask was inoculated with a cryoculture of the corresponding strain. The culture was cultured overnight at 37° C. with shaking at 200 rpm and was used on the next day, to inoculate an identical main culture to an OD of 0.2. The main cultures (each 30 mL of LB medium) were then incubated further under the same conditions. At an OD of 0.4 to 0.5, the main culture was covered in each case with equal volumes (30 ml) of solvent and was then incubated further.

For determination of the number of CFUs (colony-forming units), in the next tests 0.1-ml samples were taken and were diluted in sterile 0.9% NaCl solution. Suitable dilution steps were plated out on LB-agar plates. After incubation at 34° C. overnight, the colonies that had formed were counted and the CFUs were determined.

Test 1: Comparison of Toxicity Between DE2HPA and a Saturated Fatty Acid as Liquid Cation Exchanger 50% DEHPA or lauric acid (15%), in each case dissolved in LAME and with equimolar or 25 mol % loading with ALAME, as liquid cation exchanger, was contacted with an *E. coli* BL21 (DE3) strain and the influence of these two compounds on the strain's ability to form colonies, expressed in CFUs, was investigated. It had been shown in preliminary tests that lauric acid methyl ester—which owing to insufficient loading cannot function as liquid cation exchanger—is tolerated well by the strains used.

TABLE 1

| Test No. | *E. coli* strain used | Liquid cation exchanger used | Number of CFUs after 22 or 24 h relative to t = 0 h |
|---|---|---|---|
| 1a | *E. coli* BL21(DE3) | None | 244% |
| 1b | *E. coli* BL21(DE3) | DEHPA | 0% |
| 1c | *E. coli* BL21(DE3) | Lauric acid | 1.2% |

It can be seen that both liquid cation exchangers lower the number of CFUs considerably, but when lauric acid is used, in contrast to DEHPA, some viable cells are still present and the saturated fatty acid is therefore to be preferred as liquid cation exchanger.

Test 2: Comparison of Toxicity Between Branched Saturated Fatty Acids and Various Amounts of Oleic Acid as Liquid Cation Exchanger In this case two different concentrations of oleic acid were used and the volume was adjusted by adding the corresponding amount of LAME (lauric acid methyl ester).

TABLE 2

| Test No. | E. coli strain used | Liquid cation exchanger used | Number of CFUs after 22 or 24 h relative to t = 0 h |
|---|---|---|---|
| 2a | E. coli BL21(DE3) | Isononanoic acid | 0 |
| 2b | E. coli BL21(DE3) | 2-Ethylhexanoic acid | 0 |
| 2c | E. coli BL21(DE3) | LAME/25% oleic acid | 11% |
| 2d | E. coli BL21(DE3) | LAME/75% oleic acid | 18% |
| 2e | E. coli W3110 | Isononanoic acid | 0 |
| 2f | E. coli W3110 | 2-Ethylhexanoic acid | 0 |
| 2g | E. coli W3110 | LAME/25% oleic acid | 29% |
| 2h | E. coli W3110 | LAME/75% oleic acid | 17% |

It can be seen that the number of viable cells when using the unsaturated fatty acid oleic acid together with LAME is consistently far higher than when using branched saturated fatty acids.

Test 3: Comparison of Toxicity Between Linear Saturated Fatty Acids and Unsaturated Fatty Acids as Liquid Cation Exchanger In this case various amounts of an unsaturated fatty acid were compared with an unsaturated fatty acid with respect to their toxicity when used as liquid cation exchanger. Owing to the lower solubility of the unsaturated fatty acid lauric acid, this was used in smaller amount. The volumes of the various cation exchangers were compared with LAME. The number of CFUs was determined at the start, after 4.5 h and after 24 h.

Figure 2:
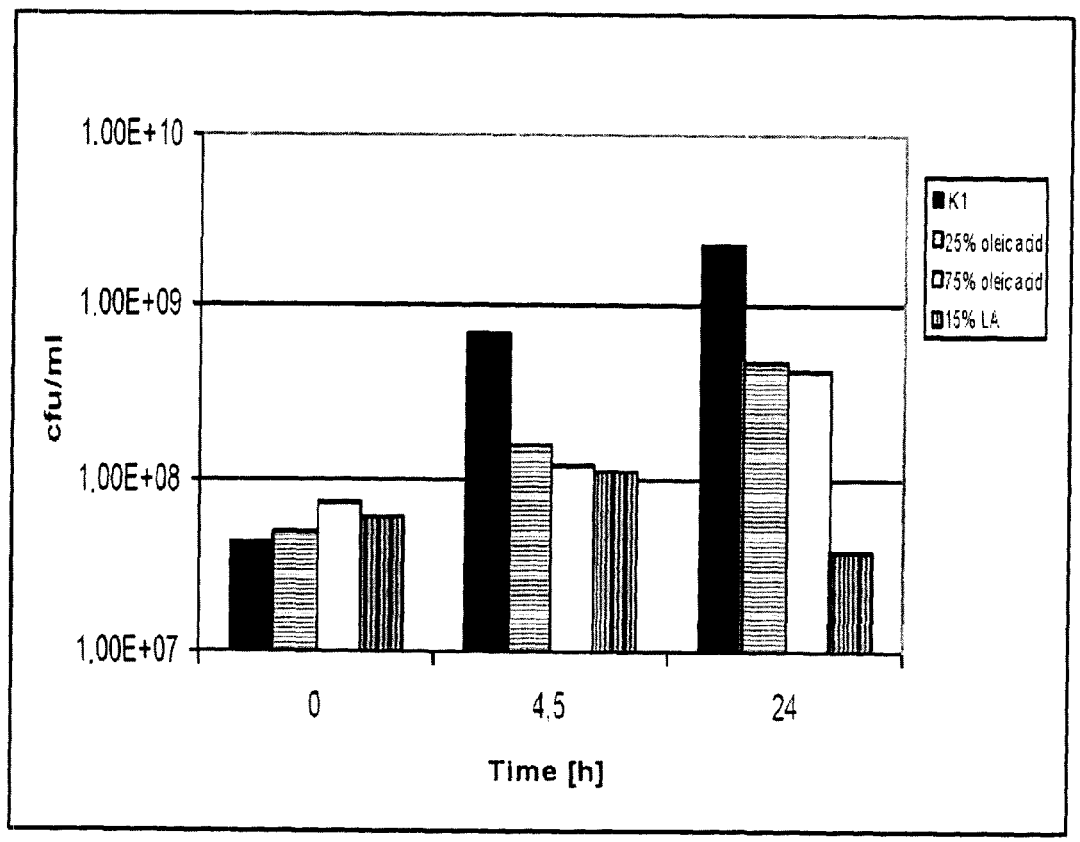
FIG. 2 shows the viability of the strain *E. coli* W3110 in the form of the number of CFUs that the strain can form in the absence of a liquid cation exchanger and in the presence of various liquid cation exchangers after 0 h, 4 h and 24 h.
Figure 3:
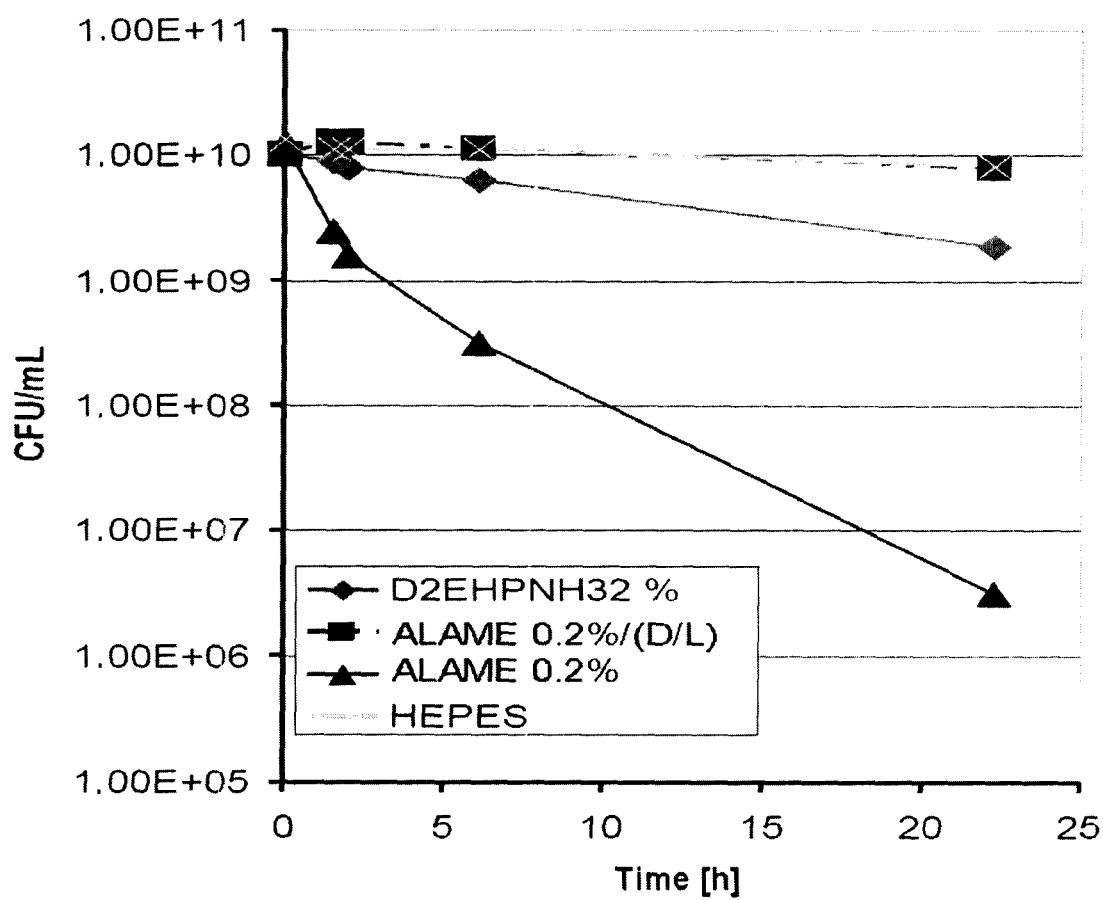
FIG. 3 shows the effect of using a liquid cation exchanger on the toxicity from the change in the live cell count of a *E. coli* W3110 strain in the presence of ALAME 0.2%, DEHPA adjusted with ammonia ("D2EHPNH3 2%") or a DEHPA/LAME mixture (2%/98%) ("D/L") in the presence of ALAME 0.2%.

As can be seen from FIG. 2, addition of the saturated fatty acid as liquid cation exchanger even in lower concentration than that of the unsaturated fatty acid brings about a decrease in CFUs, whereas in the case of the unsaturated fatty acid an increase in CFUs is recorded.

Overall, there is a decrease in toxicity with the various liquid cation exchangers investigated, in the following order: DEHPA>saturated fatty acids>unsaturated fatty acids.

EXAMPLE 3

Lowering the Toxicity of a Positively Charged Organic Compound by Contacting with a Liquid Cation Exchanger This test shows that through the presence of a liquid cation exchanger, the toxic action of a positively charged organic compound in an aqueous phase, which is fermentation broth, can be lowered, as this compound is extracted into the organic phase.

The basic experimental procedure corresponded to that in example 1.

As ALAME 0.2% (w/v), dissolved in aqueous systems, has bactericidal action, this test was repeated in combination with D2EHPNH3/LAME 2/98% (w/w) in the shaking flask, where D2EHPNH3 means D2EHPA loaded quantitatively with ammonium. By using the liquid ion exchanger, the transfer of ALAME into the organic phase is improved, so that its concentration in the aqueous phase, in which the cells are also located, decreases. In order to reduce toxic action caused by D2EHPA, low concentrations of 2% (w/w) D2EHPNH3 were used.

The bacteria were first resuspended in 5 mL (corresponds to half the buffer volume). A further 5 mL of buffer optionally with addition of 0.4% (w/v) ALAME and then optionally with 5 mL D2EHPNH3/LAME 2/98% (w/w) were vortexed for 1 min at 3000 rpm. This solution was added to the bacterial suspension in the shaking flask and mixed. Then the first sampling was carried out.

Figure 4:
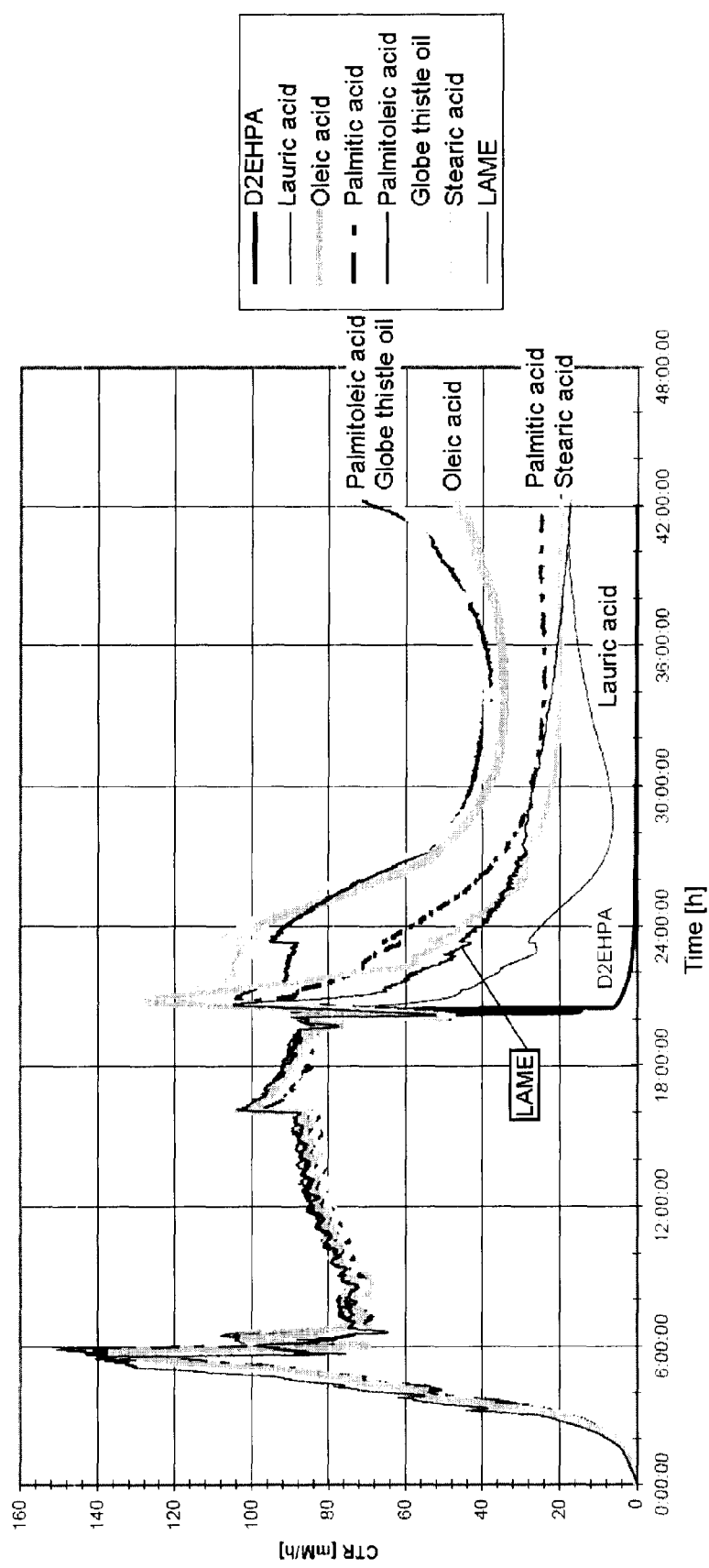
FIG. 4 shows the effect of various liquid cation exchangers on the OTR of aminolauric acid methyl ester producing *E. coli* strain. The experiment was carried out as described in example 4.
Figure 5:
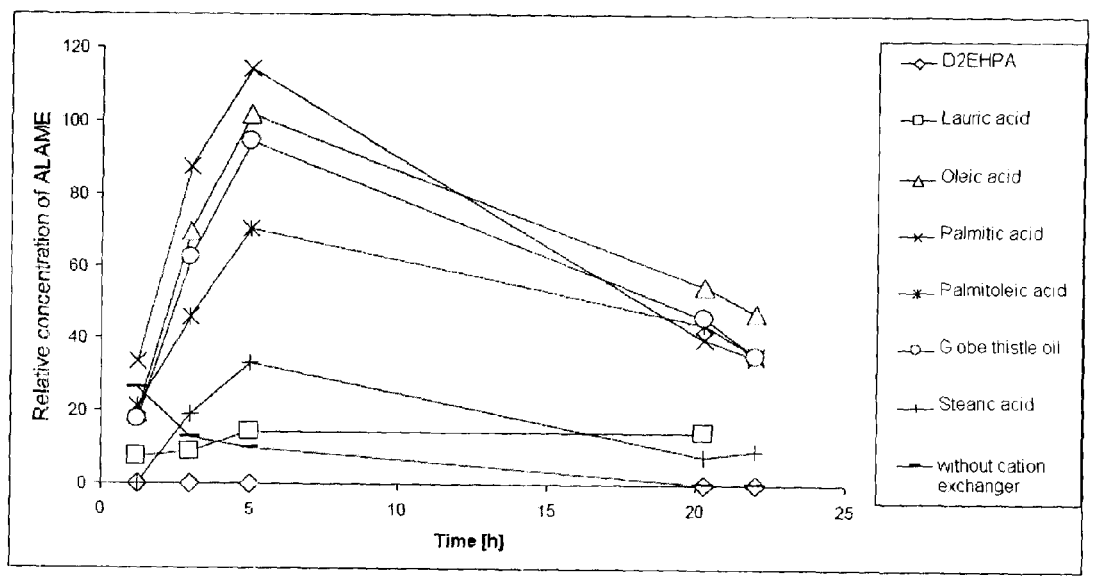
FIG. 5 shows the influence of various liquid cation exchangers on the yield of aminolauric acid methyl ester produced by an *E. coli* strain with suitable genetic modification. The experiment was carried out as described in example 4.

The solution had a foamy consistency at the start of the tests, but this had disappeared at the 2nd sampling in both tests. The abbreviation "D/L" was used for D2EHPNH3 (ammonia-laden D2EHPA)/LAME 2/98% (w/w). Between the samplings $t_0$ and $t_{1.5}$ h, the CFU/mL count increased by 34.3%. From sampling ($t_{1.5}$) up to the last sampling ($t_{22}$) the CFU/mL count decreased by 54.9%. Compared to the assay with D2EHPNH3/LAME 2/98% (w/w) without addition of ALAME 0.2% (w/v), the viable cell count after 22 h was 4.5 times higher and at 3.4% was not significantly lower than the mean value of the control assays in HEPES buffer (see FIG. 4). Compared to the assay with ALAME 0.2% (w/v) in the shaking flask, without addition of an organic phase, the CFU/mL count was 2800 times higher.

It can be seen that the presence of the liquid cation exchanger lowers the toxicity of the positively charged compound, found in this case from the number of CFUs remaining.

EXAMPLE 4

Comparative Tests for the Toxicity of Various Liquid Cation Exchangers Versus an ω-Aminolauric Acid (ALA) and the Methyl Ester (ALAME) Producing Microorganism The biotransformation of lauric acid methyl ester to aminolauric acid methyl ester was tested in the 8-fold parallel fermentation system of DasGip with various ion exchangers.

1 L reactors were used for the fermentation. The pH probes were calibrated by means of a two-point calibration with standard solutions of pH 4.0 and pH 7.0. The reactors were filled with 300 mL water and were autoclaved for 20 min at 121° C., to ensure sterility. Then the pO2 probes were polarized overnight (for at least 6 h). On the next morning, the water was removed under the clean bench and was replaced with high-cell-density medium with 50 mg/L kanamycin and 34 mg/L chloramphenicol. Next the pO2 probes were calibrated with a single-point calibration (stirrer: 600 rpm/gassing: 10 sL/h air) and the feed, correcting-agent and induction-agent sections were cleaned by Clean-in-Place. For this, the hoses were rinsed with 70% ethanol, then with 1 M NaOH, then with sterile deionized water and finally were filled with the respective media.

The ALA and ALAME producing E. coli strain BL21 (DE3) T1r pBT10 pACYC:Duet[TAcv] was first grown from cryoculture in LB medium (25 mL in a 100 mL baffle flask) with 50 mg/L kanamycin and 34 mg/L chloramphenicol overnight at 37° C. and 200 rpm for approx. 18 h. Then in each case 2 mL is inoculated in high-cell-density medium (glucose 15 g/L (30 mL/L of a separately autoclaved 500 g/L stock solution with 1% $MgSO_4*7H_2O$ and 2.2% $NH_4Cl$), $(NH_4)_2SO_4$ 1.76 g/L, $K_2HPO_4$ 19.08 g/L, $KH_2PO_4$ 12.5 g/L, yeast extract 6.66 g/L, trisodium citrate dihydrate 11.2 g, ammonium iron citrate solution 17 mL/L of a separately autoclaved 1% stock solution, trace element solution 5 mL/L of separately autoclaved stock solution (HCl (37%) 36.50 g/L, $MnCl_2*4H_2O$ 1.91 g/L, $ZnSO_4*7H_2O$ 1.87 g/L, ethylenediaminetetraacetic acid dihydrate 0.84 g/L, $H_3BO_3$ 0.30 g/L, $Na_2MoO_4*2H_2O$ 0.25 g/L, $CaCl_2*2H_2O$ 4.70 g/L, FeSO$_4$*7H$_2$O 17.80 g/L, CuCl$_2$*2H$_2$O 0.15 g/L)) (3 times each 25 mL in a 100 mL baffle flask) with 50 mg/L kanamycin and 34 mg/L chloramphenicol and incubated at 37° C./200 rpm for a further 6 h.

The 3 cultures were combined in a shaking flask and the optical density was determined as 7.2. For inoculating the reactors at an optical density of 0.1, in each case 4.2 mL was taken up in a 5 mL syringe and the reactors were inoculated by cannula through a septum.

The following standard programme was used:

| DO controller | | | pH controller | | |
|---|---|---|---|---|---|
| Preset | | 0% | Preset | | 0 ml/h |
| P | | 0.1 | P | | 5 |
| Ti | | 300 s | Ti | | 200 s |
| Min | | 0% | Min | | 0 mLL/h |
| Max | | 100% | Max | | 40 mL/h |
| N (rotation) | from | to | XO2 (gas mixture) | from | to | F (gas flow) | from | to |
| Growth and biotransformation | 0% | 30% 400 rpm 1500 rpm | Growth and biotransformation | 0% 21% | 100% 21% | Growth and biotransformation | 15% 6 sL/h | 80% 72 sL/h |
| Script | | | | | |
| Trigger sharp | | | 31% DO (1/60 h) | | |
| IPTG induction | | | 2 h after feed start | | |
| Feed trigger | | | 50% DO | | |
| Feed rate | | | 3 [mL/h] | | |

The experiment carried out can be divided into two phases, growing, in which the cells are to reach a specified optical density, and the subsequent biotransformation, in which the expression of the genes necessary for the biotechnological processes of production of ALAME was induced. The pH values were adjusted on one side with ammonia (12.5%) to pH 6.8. During growing and biotransformation, the dissolved oxygen (DO) in the culture was controlled at 30% by means of the stirrer rotary speed and the gassing rate. Fermentation was carried out as fed batch, wherein feed start, 5 g/Lh glucose feed (500 g/L glucose with 1% MgSO$_4$*7H$_2$O and 2.2% NH$_4$Cl), was triggered by a DO peak. At feed start, the temperature was also lowered from 37° C. to 30° C. Expression of transaminase was induced 2 h after feed start by the automatic addition of IPTG (1 mM). Induction of the alk-genes was effected by manual addition of DCPK (0.025% v/v) 10 h after feed start. The optical density of the culture broths was determined before the start of biotransformation.

The biotransformation phase started 14 h after feed start. For this, 150 mL of a mixture of lauric acid methyl ester and the respective ion exchanger (10% w/w) were added as batch to the fermentation broth. Di(2-ethylhexyl-)phosphoric acid (DEHPA), lauric acid, oleic acid, palmitic acid, palmitoleic acid, stearic acid and a mixture of free fatty acids from the saponification of globe thistle oil were used as ion exchangers. In order to make an amino group donor available for the transaminase, 10.7 mL of an alanine solution (125 g/L) was added to the fermentation broth simultaneously with addition of the organic phase. For sampling, 2 mL of fermentation broth was taken from the vessel and a portion of this was diluted 1/20 in an acetone-HCl mixture (c(HCl)=0.1 mol/L) and extracted. Samples were taken from all 8 reactors at 1.25 h, 3 h, 5 h, 20 h, 22 h and 25 h after the start of biotransformation. The oxygen transfer rate (OTR) and carbon transfer rate (CTR) were determined during the fermentation by exhaust gas analysis on the DasGip systems. The fermentation was ended 22 h after the start of biotransformation.

The quantification of ALA, ALAME, DDS, DDSME, LS, LAME, HLS, HLSME, OLS and OLSME in fermentation samples was carried out by means of LC-ESI/MS$^2$ with external calibration for all analytes and using the internal standard aminoundecanoic acid (AUD).

The following equipment was used:
HPLC System 1260 (Agilent; Böblingen) with autosampler (G1367E), binary pump (G1312B) and column furnace (G1316A)
TripelQuad 6410 mass spectrometer (Agilent; Böblingen) with ESI source
HPLC column: Kinetex C18, 100×2.1 mm, particle size: 2.6 μm, pore size 100 Å (Phenomenex; Aschaffenburg)
Precolumn: KrudKatcher Ultra HPLC in-line filter; 0.5 μm filter depth and 0.004 mm inside diameter (Phenomenex; Aschaffenburg)

The samples were prepared by pipetting 1900 μL of solvent (acetone/0.1 N HCl mixture=1:1) and 100 μL of sample into a 2-mL reaction vessel. The mixture was vortexed for approx. 10 seconds and then centrifuged at approx. 13000 rpm for 5 min. The clear supernatant was removed with a pipette and was analysed after appropriate dilution with diluent (80% (v/v) ACN, 20% doubly-distilled water (v/v), +0.1% formic acid). 100 μL ISTD was added by pipette per 900 μL of sample (10 μL at a sample volume of 90 μL).

HPLC separation was carried out with the aforementioned column and/or precolumn. The injection volume was 0.7 μL, column temperature 50° C., and flow rate 0.6 mL/min. The mobile phase consisted of eluent A (0.1% (v/v) aqueous formic acid) and eluent B (acetonitrile with 0.1% (v/v) formic acid). The following gradient profile was used

| Time [min] | Eluent A [%] | Eluent B [%] |
|---|---|---|
| 0 | 77 | 23 |
| 0.3 | 77 | 23 |

| Time [min] | Eluent A [%] | Eluent B [%] |
|---|---|---|
| 0.4 | 40 | 60 |
| 2.5 | 40 | 60 |
| 2.6 | 2 | 98 |
| 5.5 | 2 | 98 |
| 5.6 | 77 | 23 |
| 9 | 77 | 23 |

ESI-MS² analysis was carried out in positive mode with the following parameters of the ESI source:
Gas temperature 280° C.
Gas flow 11 L/min
Sprayer pressure 50 psi
Capillary voltage 4000 V
Detection and quantification of the individual compounds was carried out with the following parameters, in each case using one product ion as qualifier and one as quantifier:

| Analyte | Precursor ion [m/z] | Product ion [m/z] | Residence time [ms] | Collision energy [eV] |
|---|---|---|---|---|
| DDSME | 245.2 | 167.1 | 25 | 6 |
| DDSME | 245.2 | 149.1 | 50 | 8 |
| HLSME | 231.3 | 181.2 | 15 | 2 |
| HLSME | 231.3 | 163.2 | 25 | 5 |
| DDS | 231.2 | 213.2 | 50 | 0 |
| DDS | 231.2 | 149.1 | 25 | 9 |
| ALAME | 230.3 | 198.1 | 25 | 10 |
| ALAME | 230.3 | 163.2 | 15 | 10 |
| OLSME | 229.2 | 197.2 | 50 | 0 |
| OLSME | 229.2 | 161.1 | 25 | 5 |
| HLS | 217.2 | 181.2 | 35 | 0 |
| HLS | 217.2 | 163.1 | 20 | 4 |
| OLS | 215.2 | 161.2 | 25 | 0 |
| OLS | 215.2 | 95.2 | 60 | 13 |

Results

If DEHPA is used as cation exchanger as described in the prior art, immediately after addition of the compound to the culture there is intrusion of the OTR. The curve drops to 0 within a short time, which indicates that metabolically active cells are no longer present in the culture. DEHPA is thus highly toxic to cells.

If lauric acid is used as liquid cation exchanger instead of DEHPA, there is admittedly also intrusion of the OTR, but it is less pronounced, and in the course of the next 22 h the cells recover and display increasing metabolic activity. Lauric acid is accordingly far less toxic than DEHPA.

Even much better results can be observed when saturated fatty acids with longer carbon chains are used. If palmitic and stearic acid are used, the decrease of the OTR curve is much shallower than when lauric acid or even DEHPA is used. It can be concluded from this that these fatty acids are far less toxic.

The use of unsaturated fatty acids such as palmitoleic acid, saponified globe thistle oil (contains mainly linoleic acid) and oleic acid leads, surprisingly, to even better results. These fatty acids show, surprisingly, even lower toxicity than the saturated fatty acids.

REFERENCES

J. Sangster, *Octanol-Water Partition Coefficients: Fundamental and Physical Chemistry*, Vol. 2 of *Wiley Series in Solution Chemistry*, John Wiley & Sons, Chichester, 1997

Asano, Y., Fukuta, Y., Yoshida, Y., and Komeda, H. (2008): The Screening, Characterisation, and Use of w-Laurolactam Hydrolase: A New Enzymatic Synthesis of 12-Aminolauric Acid, *Biosc. Biotechn. Biochem.*, 72 (8), 2141-2150

DE10200710060705 (2007): Recombinant cells producing ω-aminocarboxylic acids or lactams thereof.

F. M. Ausubel (1995), Current Protocols in Molecular Biology. John Wiley & Sons, Inc.

A. M. Lesk (2008), Introduction to Bioinformatics, 3rd Edition

The invention claimed is:

1. A method for removing an organic compound from an aqueous solution, the method comprising:
   a) contacting an aqueous solution comprising an organic compound with a hydrophobic organic solution comprising a hydrophobic liquid cation exchanger, and
   b) separating the organic solution from the aqueous solution,
   wherein the organic compound has a formula I $NH_3^+$-A-$COOR^1$            (I), 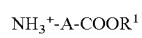

wherein $R^1$ is hydrogen, methyl, ethyl or a negative charge and A is an unsubstituted, linear alkylene group comprising at least three carbon atoms,
   wherein the liquid cation exchanger is a fatty acid, and
   wherein the contacting is performed at a temperature of 28 to 70° C.

2. The method of claim 1, wherein the contacting is performed at a pH of 6 to 8.

3. The method of claim 1, wherein a molar ratio of the liquid cation exchanger to the organic compound is at least 1.

4. The method of claim 1, wherein a volume ratio of the organic solution to the aqueous solution is 1:10 to 10:1.

5. The method of claim 1, wherein the liquid cation exchanger is a fatty acid comprising more than 12 carbon atoms.

6. The method of claim 1, wherein the liquid cation exchanger is an unsaturated fatty acid.

7. The method of claim 1, wherein the aqueous solution further comprises a biological catalyst agent having catalytic activity.

8. The method of claim 7, wherein the biological agent is a cell.

9. The method of claim 7, wherein the presence of the organic compound has an adverse effect on the catalytic activity of the biological agent having catalytic activity.

10. The method of claim 1, wherein the organic solution further comprises an organic solvent.

11. The method of claim 10, wherein
    the organic solution comprises as the liquid cation exchanger 20 to 80 vol % of oleic acid, and as the organic solvent lauric acid methyl ester,
    the organic compound is 12-aminolauric acid methyl ester, and
    a bacterial cell is present in the aqueous solution, wherein the bacterial cell comprises a recombinant alkane monooxygenase and a recombinant transaminase.

12. A reaction mixture comprising an aqueous solution and a hydrophobic organic solution, wherein the hydrophobic organic solution comprises a fatty acid as a liquid cation exchanger,
    and wherein the aqueous solution comprises a compound of formula (I)

$NH_3^+$-A-$COOR^1$            (I), 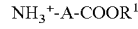

wherein $R^1$ is hydrogen, methyl, ethyl or a negative charge and A is an unsubstituted, linear alkylene group comprising at least three carbon atoms, and wherein the aqueous solution further comprises a cell comprising a recombinant alkane monooxygenase and a recombinant transaminase.

13. The method of claim 1, wherein A in formula I is an unsubstituted, linear alkylene group comprising at least eight carbon atoms.

14. The method of claim 1, wherein the contacting is performed at a temperature of 30 to 37° C.

15. The method of claim 1, wherein the contacting is performed at a pH of 6.2 to 7.2.

16. The method of claim 1, wherein the liquid cation exchanger is a fatty acid comprising 14 to 22 carbon atoms.

17. The method of claim 1, wherein the liquid cation exchanger is a fatty acid comprising 16 to 18 carbon atoms.

18. The method of claim 1, wherein the liquid cation exchanger is oleic acid or erucic acid.

* * * * *